United States Patent
Lv et al.

(10) Patent No.: US 11,718,869 B2
(45) Date of Patent: Aug. 8, 2023

(54) METHOD AND KIT FOR DETERMINING GENOME INSTABILITY BASED ON NEXT GENERATION SEQUENCING (NGS)

(71) Applicant: ZHENYUE BIOTECHNOLOGY JIANGSU CO., LTD., Taizhou (CN)

(72) Inventors: Fang Lv, Taizhou (CN); Huiting Yan, Taizhou (CN); Yaxi Zhang, Taizhou (CN); Shiqi Zheng, Taizhou (CN); Yiqian Liu, Taizhou (CN); Jianing Yu, Taizhou (CN); Hong Lv, Taizhou (CN); Weizhi Chen, Taizhou (CN); Shan Zheng, Taizhou (CN); Ji He, Taizhou (CN); Bo Du, Taizhou (CN)

(73) Assignee: ZHENYUE BIOTECHNOLOGY JIANGSU CO., LTD., Taizhou (CN)

( * ) Notice: Subject to any disclaimer, the term of this patent is extended or adjusted under 35 U.S.C. 154(b) by 0 days.

(21) Appl. No.: 17/200,941

(22) Filed: Mar. 15, 2021

(65) Prior Publication Data
US 2022/0049297 A1    Feb. 17, 2022

Related U.S. Application Data

(63) Continuation of application No. PCT/CN2021/074741, filed on Feb. 2, 2021.

(30) Foreign Application Priority Data

Aug. 12, 2020  (CN) .......................... 202010804330.1

(51) Int. Cl.
| | |
|---|---|
| C12Q 1/6858 | (2018.01) |
| C12Q 1/686 | (2018.01) |
| G16B 40/00 | (2019.01) |
| G16B 20/50 | (2019.01) |
| G16B 30/10 | (2019.01) |
| G16B 20/10 | (2019.01) |
| G16B 40/20 | (2019.01) |
| G06N 20/00 | (2019.01) |

(52) U.S. Cl.
CPC .......... *C12Q 1/6858* (2013.01); *C12Q 1/686* (2013.01); *G16B 20/10* (2019.02); *G16B 20/50* (2019.02); *G16B 30/10* (2019.02); *G16B 40/00* (2019.02); *G06N 20/00* (2019.01); *G16B 40/20* (2019.02)

(58) Field of Classification Search
CPC ........ G16B 30/10; G16B 40/00; G16B 20/50; G16B 40/20; G06N 20/00
See application file for complete search history.

(56) References Cited

U.S. PATENT DOCUMENTS

2014/0363521 A1*  12/2014  Abkevich ............ A61K 33/243
                                                   424/649

FOREIGN PATENT DOCUMENTS

CN        108588194 A       9/2018

OTHER PUBLICATIONS

Meyerson et al., Advances in understanding cancer genomes through second-generation sequencing, 2010, Nature Reviews Genetics, 11, p. 685-696 (Year: 2010).*
Telli et al., Homologous Recombination Deficiency (HRD) Score Predicts Response to Platinum-Containing Neoadjuvant Chemotherapy in Patients with Triple-Negative Breast Cancer, 2016, Clin Cancer Res, 22(15), p. 3764-3773 (Year: 2016).*
Timms et al., Association of BRCA1/2 defects with genomic scores predictive of DNA damage repair deficiency among breast cancer subtypes, 2014, Breast Cancer Research, 16:475, p. 1-9 (Year: 2014).*
Kemal et al., Genome-Wide Somatic Alterations in Multiple Myeloma Reveal a Superior Outcome Group, 2020, ASCO, Journal of Clinical Oncology, p. 1-12; Pub. Date: Jul. 22, 2020 (Year: 2020).*
Zhenhua Yu, Study on detection algorithms for tumor genomic copy number alterations based on next-generation sequencing, University of Science and Technology of China, A dissertation for doctor's degree, May 2016, pp. 1-104.
Adam B. Olshen, et al., Circular binary segmentation for the analysis of array-based DNA copy number data, Biostatistics, 2004, pp. 557-572, vol. 5 No. 4.

* cited by examiner

*Primary Examiner* — Mary K Zeman
*Assistant Examiner* — Kaitlyn L Minchella
(74) *Attorney, Agent, or Firm* — Bayramoglu Law Offices LLC (57) ABSTRACT

A method and a kit for determining genome instability based on next generation sequencing (NGS) are disclosed. The new method is used to determine whether there is homologous recombination defect by calculating a comprehensive value of one or more of pathogenic germline and somatic mutations, such as SNV, indels, and CNVs, and Biallelic germline and somatic mutations, pathogenic mutational signature, copy number variation (CNV) in homologous recombination repair (HRR) gene, genomic structural variation and genome instability. The genomics DNA is interrupted and added with an A adapter; then corresponding polymerase chain reaction (PCR) is conducted, and Whole genome sequencing is performed; the hybrid capture is conducted with designed probes of HRR genes and SNPs, and a captured DNA library is subjected to amplification and library sequencing; and then professional bioinformatics software is used for evaluation to determine the homologous recombination deficiency (HRD) status.

5 Claims, 3 Drawing Sheets

METHOD AND KIT FOR DETERMINING GENOME INSTABILITY BASED ON NEXT GENERATION SEQUENCING (NGS)

CROSS REFERENCE TO THE RELATED APPLICATIONS

This application is a continuation application of the International Application PCT/CN2021/074741, filed on Feb. 2, 2021, which is based upon and claims priority to Chinese Patent Application No. 202010804330.1, filed on Aug. 12, 2020, the entire contents of which are incorporated herein by reference.

TECHNICAL FIELD

The present invention relates to the technical field of molecular diagnosis, and more particularly, to a method and a kit for determining genome instability based on next generation sequencing (NGS).

BACKGROUND

Homologous recombination refers to the recombination among non-sister chromatids or among or within DNA molecules with homologous sequences on the same chromosome. Homologous recombination allows a damaged chromosome to repair itself through the same DNA on another undamaged chromosome, which ensures the integrity of a genome. When there is homologous recombination deficiency (HRD) due to homologous recombination gene mutation in cells, the cells cannot repair DNA itself through homologous recombination. For example, well-known breast cancer-associated genes BRCA1 and BRCA2 are homologous recombination proteins. Mutation of BRCA1 and BRCA2 genes in an individual will result in a lifetime risk of 87% for developing breast cancer, a risk of more than 40% for developing ovarian cancer, and an earlier age of onset.

Poly ADP-ribose polymerase (PARP) is a DNA repair enzyme that plays a key role in a DNA repair pathway. When DNA is damaged and broken, PARP is activated. As a molecular receptor of DNA damage, PARP can recognize and bind to a DNA break position, and then activate and catalyze the poly-ADP ribosylation of a receptor protein to participate in a DNA repair process. Therefore, a PARP inhibitor is a PARP-targeted anti-cancer drug, which can cause synthetic lethality of tumor cells that result in homologous recombination repair (HRR) function defects, but does not affect normal cells, thereby producing a highly-selective anti-tumor effect. Studies have found that tumor cells with BRCA mutations are highly sensitive to PARP inhibitors.

HRR pathway is very complicated, and it is relatively difficult to detect mutations therein. Therefore, it is of great significance to establish an accurate, reliable, and sensitive detection method. However, current detection methods for homologous recombination pathway genes fail to achieve full coverage of genes. Current detection methods do not consider the intron regions of homologous recombination genes, let alone other genes in a homologous recombination pathway. For example, in a method of detecting BRCA1 and BRCA2 gene mutations, targeted sequencing of HRR genes mainly involves the exon regions of BRCA1 and BRCA2 genes, and does not take into account the intron regions of BRCA1 and BRCA2 and other genes in a pathway. The exons of BRCA1 and BRCA2 have a length of 40 nt to 4931 nt, and the introns have a length of 92 nt to 14,544 nt. The deletion of large fragments less than 50 nt on BRCA1 and BRCA2 has been shown to affect the normal functions of BRCA1 and BRCA2. For a gene that is short in exon length and has excessively long introns on both sides, capturing the entire gene is superior to capturing only the exon region, which increases the accuracy of the detection of cnv and large fragment deletion. In addition, studies have shown that the ATM gene on a homologous recombination pathway has the functions of cell cycle arrest and DNA repair, and the ATM protein has thus become one of the targets of PARP inhibitors. A protein produced by RAD51 binds to single-stranded and double-stranded DNAs and catalyzes the recognition and strand exchange among homologous DNAs, thereby playing an important role in an HRR process. The failure of RAD51 foci formation is one of the characteristics of cells that have failed HRR pathways. Failure of every HRR gene may lead to genome instability.

In addition to the detection of gene mutations in a homologous recombination pathway, genomic structural variation, a phenotype of HRR defects, is also one of the targets of PARP inhibitors. At present, assessment is mainly conducted by calculating a weighted value of one or more values of loss of heterozygosity (LOH), telomeric allelic imbalance (TAI), large-scale state transition (LST), large-fragment INDEL variation, copy number variation (CNV) score, and tumor mutational burden (TMB). The current technology mainly adopts targeted sequencing to obtain the above values. Targeted sequencing can provide a high sequencing depth, but has the disadvantages of low capture efficiency and insufficient probe density due to common repetitive sequences in telomeric regions. Moreover, targeted sequencing is difficult to achieve the capture of genomic structural variation with a small interval and CNV in telomeric regions. The identification of copy number (CN) in telomeric regions plays a vital role in the calculation of a genomic structural variation score. Mutational signatures are a characteristic set of mutation types caused by specific mutagenesis processes where Signature 3 has been proven to be related to the inactivation of BRCA2. Currently, in existing products, no mutational signatures are added as a method to assist in determining the function and activity of HRR pathway. Biallelic pathogenic mutation refers to the loss of functions of two genotypes of the same gene due to CNVs or point mutations. Patients with biallelic pathogenic mutations have higher LST scores compared with patients with no biallelic pathogenic mutations. At present, existing products do not involve the calculation of a biallelic pathogenic mutation load, which results in low sensitivity and poor specificity. In view of this, the present invention provides a method and a kit for determining genome instability based on NGS.

SUMMARY

The detection of HRD in the prior art has the following shortcomings:
1. Other genes on a homologous recombination pathway are not considered in the detection of HRD.
2. In existing products, no mutational signatures are added as an effective means to assist in determining the function and activity of HRR pathway.
3. Existing products do not involve the calculation of a biallelic pathogenic mutation load, which results in low sensitivity and poor specificity.
4. The detection of BRCA1/2 in the prior art fails to achieve full coverage of genes, which mainly involves the exon regions of the two genes of BRCA1/2 and does not consider the intron regions of BRCA1/2.

5. At present, when targeted sequencing is used to capture telomeric regions, problems of low capture efficiency and insufficient probe density are present due to common repetitive sequences in telomeric regions. Therefore, targeted sequencing is difficult to achieve the capture of genomic structural variation with a small interval and CNV in telomeric regions.

The present invention provides a method and a kit for determining genome instability based on NGS. The present invention provides a test kit for determining whether there is a lack of homologous recombination function in a patient by calculating a comprehensive value of one or more of pathogenic point mutation or Indel mutation of HRR gene, biallelic pathogenic mutation burden of HRR gene, mutational signature of HRR gene, CNV of HRR gene, CN burden of HRR gene, and genomic structural variation.

The pathogenic point mutation or Indel mutation of HRR gene, biallelic pathogenic mutation burden of HRR gene, mutational signature of HRR gene, CNV of HRR gene, and CN burden of HRR gene are obtained by sequencing tumor samples and normal samples captured by probes designed with related target genes (gene-panel).

The genomic structural variation is obtained by subjecting an obtained genome sequence of a tumor sample to targeted sequencing (single-nucleotide polymorphism (SNP)-panel (SNP probes)) and whole-genome sequencing (WGS).

Probes for the SNP-Panel are designed according to the following steps:
1) screening regions for designing genome probes as follows: removing gaps (genomic inaccessible region) and regions difficult to map on the genome, and removing genomic regions that have a GC content higher than 60% and less than 30% and a length of 200 bp;
2) removing regions that have a length of 120 bp and include three or more loci with an Asian heterozygosity greater than 0.5;
3) screening snp loci in a 1,000 genomes database in the regions for designing probes as follows: determining whether an Asian heterozygosity is greater than 0.5; determining whether Hardy-Weinberg equilibrium is reached; and extending an snp locus by 100 bp on both sides and aligning a resulting sequence with the genome, with not more than 10 alignment positions.

The evaluation of the genomic structural variation of a tumor sample is mainly achieved by a sum of one or more of allelic imbalance (AI) scores in different regions of a genome and LST scores, and the bioinformation process is executed by the following steps:
1) aligning sequences of a tumor sample and a baseline sample that are determined by targeted sequencing with a genome to obtain a B-allele frequency (BAF) and a CN of heterozygous loci in a targeted region of the tumor sample;
2) screening out a heterozygous locus of the sample itself and acquiring an allele frequency of the heterozygous locus;
3) for genome sequencing data of targeted sequencing, using a circular binary segmentation (CBS) method to segment based on the CN to obtain regions of different CN sizes on the genome, and based on the BAF, further segment the regions obtained from the segmentation based on the CN to obtain continuous genomic regions with equivalent CNs and BAFs;
4) according to results in 3), determining AI scores of regions in the genome other than centromeres and telomeres;
5) aligning sequences of the tumor and baseline samples obtained from WGS with the genome to obtain a CN of the tumor sample at a whole genome scale;
6) using results in step 5) to determine AI scores of telomeric regions and LST scores.

Calculation of the mutational signatures of HRR gene for a tumor sample is mainly based on statistics of targeted sequencing data of a homologous recombination gene, mainly including the following steps:
1) identifying single-nucleotide variants (SNVs) and annotating at a genetic level;
2) screening according to annotation results; and
3) using software (sigma (software for calculating point mutational signatures)) to analyze mutational signatures.

The pathogenic point mutation or Indel mutation of HRR gene is identified through targeted sequencing of homologous recombination gene.

The biallelic pathogenic mutation burden of HRR gene is obtained mainly by counting the CN and allele frequency of HRR gene.

The CN burden of HRR gene is obtained by calculating the number of genes whose CNVs exceed a threshold.

The present invention provides a method for determining genome instability based on NGS, including the following steps:
A) diluting formalin-fixed and paraffin-embedded tissue sample DNA (FFPE DNA) and blood sample DNA (BC DNA) to a concentration of 6 ng/µL, and using an interrupter (manufacturer: Covaris, model: M220) to treat the DNA to obtain fragmented DNA;
B) adding the fragmented DNA to an end repair/A-tailing reaction system for a first round of polymerase chain reaction (PCR) to obtain A-tailed fragmented DNA; after the reaction is completed, adding a prepared ligation system to a resulting PCR system for a second round of PCR; and after the reaction is completed, conducting magnetic bead purification to obtain a purified ligation product;
C) adding a prepared amplification system to the purified ligation product, and conducting PCR according to the following reaction procedure: 98° C. for 45 s, 1 cycle; 98° C. for 15 s, 60° C. for 30 s, 72° C. for 30 s, N cycle; and 72° C. for 1 min, 1 cycle; terminating the reaction at 8° C., and conducting magnetic bead purification to obtain a DNA library; using a nucleic acid concentration detector to quantify an FFPE DNA library ≥350 ng and a BC DNA library ≥200 ng; and using a 2100 bioanalyzer to analyze the libraries, where, main peaks should be located between 150 bp to 500 bp;
D) hybrid capture: mixing the FFPE DNA library and the BC DNA library at a mass ratio of 1:1, adding human Cot-1 DNA and blocking sequences to a resulting DNA library mixture, and subjecting a resulting DNA library mixture to evaporation drying with a vacuum centrifugal concentrator;
E) adding a DNA hybridization system to a resulting DNA library obtained from the evaporation drying, shaking a resulting mixture for thorough mixing, and subjecting the mixture to centrifugation, incubation at room temperature, and hybridization at 95° C. for 30 s and then at 65° C. for 4 h to obtain a captured library;
F) amplification of the captured library: adding a library amplification reaction system to the captured library, and conducting PCR according to the following reaction procedure: 98° C. for 45 s, 1 cycle; 98° C. for 15 s, 60° C. for 30 s, 72° C. for 30 s, 14 cycles; and 72° C. for 1 min, 1 cycle; and subjecting an amplification product to magnetic bead purification;

G) library sequencing: mixing the FFPE DNA library and the BC DNA library at a ratio of 6:1, subjecting a resulting mixture to capturing with SNP probes, and using a gene sequencer to conduct computer sequencing on a captured product; after the computer sequencing is completed, processing obtained sequencing data with software to obtain processed sequences that have adapter, primer and low-quality parts removed; using NGS data alignment software to align pre-processed WGS data and the above processed sequences with a human reference genome to obtain position information of each sequence and alignment quality information; and using software to compare obtained results for quality evaluation.

In the above detection method, in the step of end repair/A-tailing reaction, a reaction system for the first round of PCR may include: 2 μL of end repair enzyme, 10 μL of end repair buffer, and 48 μL of nuclease-free water; the first round of PCR may be conducted at 20° C. for 30 min and at 65° C. for 30 min and then terminated at 4° C.; a reaction system for the second round of PCR may include: 30 μL of DNA ligation buffer, 3 μL of DNA ligase, 0.5 μL of ligation enhancer, 2.5 μL of adapter, and 14 μL of nuclease-free water; and the second round of PCR may be conducted at 20° C. for 15 min and then terminated at 4° C.

In the above detection method, in step C), if the purified ligation product is the FFPE DNA, N is 8; if the purified ligation product is the BC DNA, N is 6; and the amplification system in step C) may include 20 μL of the purified ligation product, 25 μL of a high-fidelity hot-start enzyme mixture, and 5 μL of library amplification primers.

In the above detection method, the DNA hybridization system may include 2.7 μL of hybridization buffer, 8.5 μL of hybridization buffer enhancer, 4.5 μL of DNA capture probes, and 1.3 μL of nuclease-free water.

In the above detection method, the library amplification reaction system may include 25 μL of a high-fidelity hot-start enzyme mixture, 5 μL of library amplification primers, and 20 μL of DNA eluted in the previous step.

In the above detection method, before sequencing, a to-be-sequenced sample is treated correspondingly, and a treating method may include the following steps: subjecting a to-be-sequenced sample to quantification with a nucleic acid concentration detector, fragment size analysis with a bioanalyzer, and molar concentration calculation; mixing 5 μL of a 4 nM to-be-sequenced sample with 5 μL of 0.2 N NaOH for fusion, and subjecting a resulting mixture to vortexing for thorough mixing, centrifugation for a short time, and denaturation at room temperature for 5 min; adding 990 μL of HT1 buffer to terminate the denaturation, and subjecting a resulting mixture to vortexing for thorough mixing and centrifugation for a short time; and diluting a denatured to-be-sequenced sample to a concentration suitable for computer sequencing.

The method for determining genome instability based on NGS described above may further include bioinformatics analysis, specifically including the following steps:

1) aligning sequences of a tumor sample and a baseline sample that are determined by targeted sequencing with a genome to obtain a BAF and a CN of heterozygous loci in a targeted region of the tumor sample;
2) screening out a heterozygous locus of the sample itself and acquiring an allele frequency of the heterozygous locus;
3) for genome sequencing data of targeted sequencing, using a CBS method to segment based on the CN to obtain regions of different CN sizes on the genome, and based on the BAF, further segment the regions obtained from the segmentation based on the CN to obtain continuous genomic regions with equivalent CNs and BAFs;
4) according to results in 3), determining AI scores of regions in the genome other than centromeres and telomeres;
5) aligning sequences of the tumor and baseline samples obtained from WGS with the genome to obtain a CN of the tumor sample at a whole genome scale; and
6) using results in step 5) to determine AI scores of telomeric regions and LST scores.

Calculation of the mutational signatures of HRR gene for a tumor sample is mainly based on statistics of targeted sequencing data of a homologous recombination gene, mainly including the following steps:

1) identifying SNVs and annotating at a genetic level;
2) screening according to annotation results; and
3) using software (sigma) to analyze mutational signatures.

The pathogenic point mutation or Indel mutation of HRR gene is identified through targeted sequencing of homologous recombination gene.

The biallelic pathogenic mutation burden of HRR gene is obtained mainly by counting the CN and allele frequency of HRR gene.

The CN burden of HRR gene is obtained by calculating the number of genes whose CNVs exceed a threshold.

The present invention also provides a kit for detecting gene mutations in a homologous recombination pathway based on NGS, and each unit of the kit includes:

1) an end repair/A-tailing reaction system: 900 μL of end repair buffer and 180 μL of end repair enzyme;
2) a ligation reaction system: 1,350 μL of DNA ligation buffer, 270 μL of DNA ligase, 45 μL of ligation enhancer, and 6 μL of adapters 01-40;
3) a PCR amplification reaction system: 485 μL of library amplification primers and 1,215 μL of high-fidelity hot-start enzyme mixture;
4) a hybrid capture reaction system: 20 μL of DNA capture probes; 14 μL of blocking sequences, 35 μL of human Cot DNA, 120 μL of hybridization buffer, 38 μL of hybridization buffer enhancer, 1,050 μL of 2× magnetic bead-washing buffer, 175 μL of 10× washing buffer 1; 105 μL of 10× washing buffer 2, 105 μL of 10× washing buffer 3, 210 μL of 10× washing buffer 4, and 350 μL of streptavidin magnetic beads; and
5) a purification reaction system: 15 mL of purification magnetic beads.

The genomic structural variation is obtained by subjecting an obtained genome sequence of a tumor sample to targeted sequencing (SNP-panel) and WGS.

Probes for the SNP-Panel are designed according to the following steps:

1) screening regions for designing genome probes as follows: removing gaps and regions with low mappability on the genome, and removing genomic regions that have a GC content higher than 60% and less than 30% and a length of 200 bp;
2) removing regions that have a length of 120 bp and include three or more loci with an Asian heterozygosity greater than 0.5;
3) screening snp loci in a 1,000 genomes database in the regions for designing probes as follows: determining whether an Asian heterozygosity is greater than 0.5; determining whether Hardy-Weinberg equilibrium is reached; and extending an snp locus by 100 bp on both sides and aligning a resulting sequence with the genome, with not more than 10 alignment positions.

The evaluation of the genomic structural variation of a tumor sample is mainly achieved by a sum of one or more of AI scores in different regions of a genome and LST scores, and the bioinformation process is executed by the following steps:

1) aligning sequences of a tumor sample and a baseline sample that are determined by targeted sequencing with a genome to obtain a BAF and a CN of heterozygous loci in a targeted region of the tumor sample;
2) screening out a heterozygous locus of the sample itself and acquiring an allele frequency of the heterozygous locus;
3) for genome sequencing data of targeted sequencing, using a CBS method to segment based on the CN to obtain regions of different CN sizes on the genome, and based on the BAF, further segment the regions obtained from the segmentation based on the CN to obtain continuous genomic regions with equivalent CNs and BAFs;
4) according to results in 3), determining AI scores of regions in the genome other than centromeres and telomeres;
5) aligning sequences of the tumor and baseline samples obtained from WGS with the genome to obtain a CN of the tumor sample at a whole genome scale; and
6) using results in step 5) to determine AI scores of telomeric regions and LST scores.

The biallelic pathogenic mutation burden of HRR gene is obtained mainly by counting the CN and allele frequency of HRR gene.

The CN burden of HRR gene is obtained by calculating the number of genes whose CNVs exceed a threshold.

Compared with the prior art, the present invention has the following technical advantages:

1. In the present invention, some exon regions of some other genes on HRR pathway are added to improve a detection sensitivity and a detection range.
2. Probes designed for capture sequencing have the problems of low capture efficiency and poor homogeneity. The genomic regions selected in the present invention are more suitable for capture sequencing and can lead to high capture efficiency and superior homogeneity in detection.
3. In the present invention, mutational signatures are added as a detection method to assist in determining the function and activity of HRR pathway.
4. In capture sequencing, signals are difficult to capture in some genomic regions, resulting in poor detection sensitivity of CNVs of these regions. WGS shows high coverage for a genome, but high-depth WGS is costly. The present invention comprehensively uses low-depth WGS and capture sequencing to develop more sensitive algorithms, which improves the sensitivity and accuracy of detection as a whole.
5. In the present invention, biallelic pathogenic mutation burden is creatively added in the prediction of HRR pathway activity, which increases the sensitivity and specificity of an algorithm.

DETAILED DESCRIPTION OF THE EMBODIMENTS

The present invention is further described below through specific examples, but those skilled in the art should understand that the examples do not limit the protection scope of the present invention in any way.

Example 1 Acquisition of Gene Sequences of Tumor Samples and Blood Cell Samples by the Kit of the Present Invention 1. Fragmentation of FFPE gDNA and BC gDNA FFPE DNA and BC DNA were diluted to a concentration of 6 ng/μL. 55 of a sample was taken for interruption with an interrupter (Covaris M220 is recommended). Device parameters for fragmentation were set according to the following table

| Parameter | Volume: 55 μL/sample |
|---|---|
| Target BP (Peak) | 200 |
| Peak Incident Power (W) | 75 |
| Duty Factor | 10% |
| Cycles per Burst | 200 |
| Treatment time (S) | 270 s (FFPE DNA)/ 6 min (BC DNA) |

2. Library Construction 2.1 End Repair/A-Tailing:

2.1.1 An end repair/A-tailing reaction system was prepared according to the following table, shaken for thorough mixing, and centrifuged for a short time.

| Component | Volume (μL) |
|---|---|
| Fragmented DNA | X |
| End repair enzyme | 2 |
| End repair buffer | 10 |
| Nuclease-free water | 48 |
| Total volume | 60 |

2.1.2 A prepared reaction system was placed on a PCR instrument, and PCR was conducted according to the following table. Note: A heated lid temperature of the PCR instrument was set to 85° C.

| Step | Temperature | Time |
|---|---|---|
| End repair/A-tailing | 20° C. | 30 min |
|  | 65° C. | 30 min |
| Termination | 4° C. | ∞ |

2.2 Adapter Ligation:

2.2.1 A ligation system was prepared according to the following table and then added to the above product, and a resulting mixture was shaken for thorough mixing and then centrifuged for a short time.

| Component | Volume (μL) |
| --- | --- |
| DNA ligation buffer | 30 |
| DNA ligase | 3 |
| Ligation enhancer | 0.5 |
| Adapter | 2.5 |
| Nuclease-free water | 14 |
| Total | 50 |

2.2.2 A prepared ligation reaction system was placed on a PCR instrument, and PCR was conducted according to the following table. Note: After a heated lid temperature of the PCR instrument was set to off and ligation reaction was completed, the next step was conducted immediately.

| Step | Temperature | Time |
| --- | --- | --- |
| Adapter ligation | 20° C. | 15 min |
| Termination | 4° C. | ∞ |

2.3 Magnetic Bead Purification 2.3.1 Purification magnetic beads were equilibrated at room temperature for at least 30 min on a multi-purpose rotating shaker before use.

2.3.2 55 μL of purification magnetic beads was added to each sample incubated above, and a resulting mixture was pipetted up and down for thorough mixing.

2.3.3 The mixture was incubated at room temperature for 5 min and then placed on a magnetic separator for about 5 min until a clear supernatant was obtained, and the supernatant was carefully removed.

2.3.4 With the centrifuge tube on the magnetic separator, 200 μL of 80% ethanol was added, a resulting mixture stood for 30 s, and a resulting supernatant was removed.

2.3.5 The above step was repeated, a 10 μL pipette tip was used to thoroughly remove residual liquid.

2.3.6 The magnetic beads were dried for 2 min to 3 min until the alcohol was completely volatilized (a front side was not reflective and a back side was dry), 21 μL of Low TE buffer was added, and a resulting mixture was pipetted up and down for thorough mixing.

2.3.7 The mixture stood at room temperature for 2 min and then placed on a magnetic separator for 1 min until a clear supernatant was obtained, and 20 μL of the supernatant was carefully pipetted to a new 8-tube strip.

2.4 Library Amplification:

2.4.1 An amplification system was prepared according to the following table and then added to a ligation product, and a resulting mixture was shaken for thorough mixing and then centrifuged for a short time.

| Component | Volume (μL) |
| --- | --- |
| Purified ligation product | 20 |
| High-fidelity hot-start enzyme mixture | 25 |
| Library amplification primers | 5 |
| Total | 50 |

2.4.2 A treated amplification system was placed on a PCR instrument, and PCR was conducted according to the following table.

| Step | Temperature | Time | Number of cycles |
| --- | --- | --- | --- |
| Pre-denaturation | 98° C. | 45 s | 1 |
| Denaturation | 98° C. | 15 s | refer to the table below |
| Annealing | 60° C. | 30 s | |
| Extension | 72° C. | 30 s | |
| Re-extension | 72° C. | 1 min | 1 |
| Storage | 8° C. | ∞ | 1 |

Sample Type and Number of Amplification Cycles:

| Sample type | Number of cycles |
| --- | --- |
| FFPE DNA | 8 |
| BC DNA | 6 |

2.5 Library Purification:

2.5.1 Purification magnetic beads were equilibrated at room temperature for at least 30 min on a multi-purpose rotating shaker before use.

2.5.2 25 μL of purification magnetic beads was added to the sample amplified above, and a resulting mixture was pipetted up and down for thorough mixing.

2.5.3 The mixture was incubated at room temperature for 5 min and then placed on a magnetic separator for about 5 min until a clear supernatant was obtained, and the supernatant was collected.

2.5.4 The supernatant was transferred to 25 μL, of purification magnetic beads, and a resulting mixture was pipetted up and down for thorough mixing.

2.5.5 The mixture was incubated at room temperature for 5 min and then placed on a magnetic separator for about 5 min until a clear supernatant was obtained, and the supernatant was removed.

2.5.6 With the centrifuge tube on the magnetic separator, 200 μL, of 80% ethanol was added, a resulting mixture stood for 30 s, and a resulting supernatant was removed.

2.5.7 The above step was repeated, a 10 μL, pipette tip was used to thoroughly remove residual liquid.

2.5.8 The magnetic beads were dried for 2 min to 3 min until the alcohol was completely volatilized (a front side was not reflective and a back side was dry), 51 μL, of Low TE buffer was added, and a resulting mixture was pipetted up and down for thorough mixing.

2.5.9 The mixture stood at room temperature for 2 min and then placed on a magnetic separator for 1 min until a clear supernatant was obtained, and 50 μL of the supernatant was carefully pipetted to a 1.5 mL centrifuge tube.

2.6 Library Quality Control:

A nucleic acid concentration detector was used for quantification: FFPE DNA library ≥350 ng and BC DNA library ≥200 ng; a bioanalyzer was used to analyze library size; and main peaks should be located between 150 bp to 500 bp.

3. Hybrid Capture 3.1 Preparation Before Experiment:

3.1.1 A vacuum centrifugal concentrator was turned on and preheated to 60° C. for later use.

3.2 Mixing of Libraries:

3.2.1 Libraries of each sample type were added to a 1.5 mL low-adsorption centrifuge tube according to the capture masses shown in the table below.

| Library type | Capture amount (ng)/library | Number of captured samples | Total amount (μg) |
|---|---|---|---|
| FFPE DNA | 83 | 12 | 1 |
| BC DNA | 83 | 12 | 1 |

3.2.2 The following two reagents were added to the DNA library mixture obtained above, and a resulting mixture was thoroughly mixed and centrifuged briefly.

| Component | Volume (μL) |
|---|---|
| Human Cot-1 DNA | 5 |
| Blocking sequences | 2 |

3.2.3 The EP tube was sealed with parafilm, and the film was punctured with a small pipette tip to form several small holes. Then the tube was placed in a vacuum centrifugal concentrator for evaporation drying (60° C., about 20 min to 1 h). Note: whether evaporation drying was completed was observed at any time.

3.3 Denaturation and Hybridization:

3.3.1 A DNA hybridization system was prepared, as shown in the table below.

| Component | Volume (μL) |
|---|---|
| Hybridization buffer | 2.7 |
| Hybridization buffer enhancer | 8.5 |
| DNA capture probes | 4.5 |
| Nuclease-free water | 1.3 |

3.3.2 The above components were thoroughly mixed and a resulting mixture was centrifuged briefly. 17 μL of the hybridization system prepared above was added to the tube with DNA library subjected to evaporation drying.

3.3.3 A resulting mixture was shaken for thorough mixing, then centrifuged for a short time, and incubated at room temperature for 5 min.

3.3.4 The above steps were repeated.

3.3.5 A liquid obtained in the above steps was transferred to a 200 μL PCR tube, then placed on a PCR instrument, and subjected to hybridization at 65° C. for 16 h according to the following hybridization procedure.

| Temperature | Time |
|---|---|
| 95° C. | 30 s |
| 65° C. | 4 h |
| 65° C. | Hold |
| Heated lid temperature: 100° C. | |

3.4 Purification after Hybridization:

3.4.1 Preparation of washing working solutions: A buffer required for each capture system was prepared as follows.

| Component | Component/ μL | Water/ μL | 1 × working solution volume/μL |
|---|---|---|---|
| 2 × magnetic bead-washing buffer | 150 | 150 | 300 |
| 10 × washing buffer 1 | 25 | 225 | 250 |
| 10 × washing buffer 2 | 15 | 135 | 150 |
| 10 × washing buffer 3 | 15 | 135 | 150 |
| 10 × washing buffer 4 | 30 | 270 | 300 |

3.4.2 300 μL of washing buffer 4 and 100 μL of washing buffer 1 were dispensed into an 8-tube strip for each capture.

3.4.3 Washing buffer 4 and washing buffer 1 should be incubated at 65° C. (heated lid temperature: 70° C.) for about 45 min before use.

3.4.4 Streptavidin magnetic beads were equilibrated at room temperature for 30 min before use.

3.4.5 50 μL of streptavidin magnetic beads was added to an 8-tube strip, and then 100 μL of magnetic bead washing buffer was added; a resulting mixture was shaken for thorough mixing and then placed on a magnetic separator for 1 min until a clear supernatant was obtained; and the supernatant was removed.

3.4.6 The above washing step was repeated 2 times.

3.4.7 The 8-tube strip was taken off from the magnetic separator, centrifuged for a short time, and then placed once again on the magnetic separator, and a 10 pipette tip was used to completely remove residual liquid at the bottom of the centrifuge tube.

3.4.8 A magnetic bead-suspending solution was prepared according to the table below and added to the washed magnetic beads.

| Component | Volume (μL) |
|---|---|
| Hybridization buffer | 2.7 |
| Hybridization buffer enhancer | 8.5 |
| Nuclease-free water | 5.8 |

3.4.9 A resulting mixture was shaken for thorough mixing, then centrifuged for a short time, transferred to a PCR tube, and then incubated in a PCR instrument at 65° C. (heated lid temperature: 70° C.) for 15 min.

3.4.10 A pipette was used to measure a hybridization solution undergoing capture overnight to ensure that a volume of the hybridization solution undergoing capture overnight was 17 μL, thus preventing loss.

3.4.11 A magnetic bead suspension incubated at 65° C. was transferred to the hybridization solution undergoing capture overnight, and a resulting mixture was pipetted up and down for thorough mixing (a temperature of the PCR tube should not be deviated from 65° C. during the entire incubation process, and in all mixing steps, a pipette was used for thorough mixing at 65° C. on a PCR instrument) and then incubated at 65° C. for 45 min in a PCR instrument (a PCR heated lid temperature was set to 70° C.), where, the mixture was pipetted up and down at the following intervals to ensure that the magnetic beads were suspended: 11 min, 11 min, 11 min, and 12 min.

3.4.12 After the incubation was completed, the solution in the PCR tube was transferred to an 8-tube strip, and 100

μL of washing buffer 1 preheated at 65° C. was added; a resulting mixture was pipetted up and down for thorough mixing and then placed on a magnetic separator for 1 min until a clear supernatant was obtained; and the supernatant was removed.

3.4.13 The 8-tube strip was taken off from the magnetic separator, quickly centrifuged for a short time (to prevent too much temperature drop), and then placed on the magnetic separator, and a 10 μL pipette tip was used to completely remove residual liquid at the bottom of the centrifuge tube.

3.4.14 150 μL of washing buffer 4 preheated at 65° C. was added, a resulting mixture was pipetted up and down for thorough mixing, incubated at 65° C. for 5 min, and then placed on a magnetic separator for 1 min until a clear supernatant was obtained, and the supernatant was removed.

3.4.15 150 μL of washing buffer 4 preheated at 65° C. was added once again, a resulting mixture was pipetted up and down for thorough mixing, incubated at 65° C. for 5 min, and then placed on a magnetic separator for 1 min until a clear supernatant was obtained, and the supernatant was removed.

3.4.16 The 8-tube strip was taken off from the magnetic separator, centrifuged for a short time, and then placed on the magnetic separator, and a 10 μL pipette tip was used to completely remove residual liquid at the bottom of the centrifuge tube. Note: During the whole hot washing process, a temperature should not be lower than 65° C. as far as possible, and the magnetic separator can be placed on a heater.

3.4.17 150 μL of washing buffer 1 at room temperature was added, a resulting mixture was shaken for 30 s, stood for 30 s, then shaken for 30 s, and stood for 30 s (2 min in total), then centrifuged for a short time, and placed on a magnetic separator for 1 min until a clear supernatant was obtained, and the supernatant was removed. The 8-tube strip was taken off from the magnetic separator, centrifuged for a short time, and then placed on the magnetic separator, and a 10 μL pipette tip was used to completely remove residual liquid at the bottom of the centrifuge tube.

3.4.18 150 μL of washing buffer 2 at room temperature was added, a resulting mixture was shaken for 30 s, stood for 30 s, then shaken for 30 s, and stood for 30 s (2 min in total), then centrifuged for a short time, and placed on a magnetic separator for 1 min until a clear supernatant was obtained, and the supernatant was removed. The 8-tube strip was taken off from the magnetic separator, centrifuged for a short time, and then placed on the magnetic separator, and a 10 μL pipette tip was used to completely remove residual liquid at the bottom of the centrifuge tube.

3.4.19 150 μL of washing buffer 3 at room temperature was added, a resulting mixture was shaken for 30 s, stood for 30 s, then shaken for 30 s, and stood for 30 s (2 min in total), then centrifuged for a short time, and placed on a magnetic separator for 1 min until a clear supernatant was obtained, and the supernatant was removed. The 8-tube strip was taken off from the magnetic separator, centrifuged for a short time, and then placed on the magnetic separator, and a 10 μL pipette tip was used to completely remove residual liquid at the bottom of the centrifuge tube.

3.4.20 21 μL of nuclease-free water was added to the centrifuge tube for elution, and a resulting mixture was shaken for thorough mixing and then used for the amplification test in the next step.

3.5 Library Amplification after Capture:

3.5.1 According to the number of captures, library amplification reaction systems were prepared according to the following table and shaken for thorough mixing.

| Component | Volume (μL) |
|---|---|
| High-fidelity hot-start enzyme mixture | 25 |
| Library amplification primers | 5 |
| DNA eluted in the previous step | 20 |

3.5.2 After centrifuged for a short time, the library amplification reaction systems were dispensed into PCR tubes, each with 30 Then, the systems were placed on a PCR instrument, and PCR was conducted according to the following table.

| Step | Temperature | Time | Number of cycles |
|---|---|---|---|
| Pre-denaturation | 98° C. | 45 s | 1 |
| Denaturation | 98° C. | 15 s | 14 |
| Annealing | 60° C. | 30 s | |
| Extension | 72° C. | 30 s | |
| Re-extension | 72° C. | 1 min | 1 |
| Storage | 8° C. | ∞ | 1 |

3.6 Purification after Amplification:

3.6.1 Purified magnetic beads were taken out and equilibrated for 30 min at room temperature for later use.

3.6.2 75 μL of purified magnetic beads was added to a 1.5 mL centrifuge tube, then 50 μL of an amplified capture DNA library supernatant was added, and a resulting mixture was shaken for thorough mixing and then incubated at room temperature for 10 min.

3.6.3 Then the mixture was placed on a magnetic separator for 1 min until a clear supernatant was obtained, and the supernatant was removed.

3.6.4 The 1.5 mL centrifuge tube was taken off from the magnetic separator, centrifuged for a short time, and then placed on the magnetic separator, and a 10 μL pipette tip was used to completely remove residual liquid at the bottom of the centrifuge tube.

3.6.5 200 μL of 80% ethanol was added for 30 s of incubation and then removed. Note: the 80% ethanol was prepared just before use. The washing was repeated once with 200 μL of 80% ethanol once.

3.6.6 The 1.5 mL centrifuge tube was taken off from the magnetic separator, centrifuged for a short time, and then placed on the magnetic separator, and a 10 μL pipette tip was used to completely remove residual liquid at the bottom of the centrifuge tube. The magnetic beads were dried at room temperature until the ethanol was completely volatilized (the magnetic beads were not reflective from a front side and was dry from a back side). Note: Excessive drying of magnetic beads will result in reduction of a DNA yield.

3.6.7 The centrifuge tube was taken off from the magnetic separator, 40 μL of ultrapure water was added, and a resulting mixture was shaken for thorough mixing and then incubated at room temperature for 2 min.

3.6.8 A resulting mixture was centrifuged for a short time and then placed on a magnetic separator for 1 min until a clear supernatant was obtained, and a capture sample was transferred to a new centrifuge tube.

3.7 Capture Quality Control: 1 µL of Each Capture was Taken for Concentration Detection by a Nucleic Acid Concentration Detector.

4. Library Sequencing 4.1 the Captured Libraries were Mixed Based on Computer Sequencing Requirements. According to the Number of Sub-Libraries Included in Each Captured Library, the Captured FFPE DNA Library and the Captured BC DNA Library were Mixed at a Ratio of 6:1.

| Capture type | Number of libraries | Addition amount (ng)/library | Total amount (ng) |
| --- | --- | --- | --- |
| FFPE DNA | 12 | 12 | 144 |
| BC DNA | 14 | 2 | 28 |

4.2 A To-be-Sequenced Sample Obtained from the Mixing was Subjected to Quantification with a Nucleic Acid Concentration Detector, Fragment Size Analysis with a Bioanalyzer, and Molar Concentration Calculation.

4.3 The To-be-Sequenced Sample was Diluted with Water to 4 nM, with a Volume of about 20 µL.

4.4 a NaOH Solution was Diluted with Water to 0.2 N, with a Volume of about 20 µL.

4.5 5 µL of the 4 nM to-be-Sequenced Sample and 5 µL of the 0.2 N NaOH were Added to a New Centrifuge Tube for Fusion, and a Resulting Mixture was Vortexed for Thorough Mixing, Centrifuged for a Short Time, and Denatured at Room Temperature for 5 Min.

4.6 990 µL of HT1 Buffer was Added to Terminate the Denaturation, and a Resulting Mixture was Vortexed for Thorough Mixing and Centrifuged for a Short Time, at which Time, the to-be-Sequenced Library had a Concentration of 20 µM.

4.7 the Denatured to-be-Sequenced Sample was Diluted to a Concentration Suitable for Computer Sequencing According to the Following Table:

| Computer sequencing concentration | Dilution method |
| --- | --- |
| 1.8 pM | 117 µL library (20 pM) + 1,183 µL HT1 |

4.8 The Above Library was Added to a Position Corresponding to a Test Reagent for Computer Sequencing.

5. Processing of Sequencing Data

The computer sequencing data were processed with software (such as Trimmomatic) to remove adapters, primers, and low-quality sequences. The NGS data alignment software bwa was used to align pre-processed raw data of WGS, SNP-panel, and gene-panel with a human reference genome to obtain position information and alignment quality information of each sequence. Then software (such as Picard) was used to compare obtained results for quality evaluation.

Example 2 Detection of Pathogenicity of Homologous Recombination Genes by the Kit of the Present Invention 1. Identification of SNV and Indel (Abbreviation for Insert and Deletion) of Homologous Recombination Genes The Mutect2 software (a software for identifying point mutations and Indel mutations) was used to analyze the NGS gene-panel alignment results of the tumor samples and normal samples obtained in Example 1 and identify somatic mutations and germline mutations in the tumor samples. The annovar software (a software for annotating genome mutations) was used to annotate somatic mutations and germline mutations identified by Mutect2. Those that meet the following criteria are pathogenic mutations:

1) the number of sequences covering a mutation locus is greater than 200;
2) mutation frequency is greater than 5%; and
3) it is recorded as a pathogenic mutation in Clinvar database, or a mutation type is fs, truncate, or splice.

2. Detection of CNVs of Homologous Recombination Genes

The cnvkit software (a software for identifying CNVs) was used to analyze the NGS gene-panel alignment results of the tumor samples and normal samples obtained in Example 1 to obtain a CN value for each gene. Determination criteria are as follows: if the value is higher than a specified threshold, it is determined as amplification; and if the value is lower than a specified threshold, it is determined as deletion.

Example 3 Calculation of a Mutational Signature Score by the Kit of the Present Invention Somatic mutations are induced by different external or internal factors, including error of DNA replication mechanisms, induction of internal or external factors, modification of DNA modification enzymes, or failure of DNA repair enzymes. Somatic mutations caused by different factors will have different combinations of mutation types, which are called mutation signatures. It has been reported that Signature 3 in the mutation signatures has a very strong correlation with homologous recombination pathway defects.

Calculation was conducted on the filtered SNV results obtained in Example 2 with the sigma software to obtain a mutational signature score related to homologous recombination.

Example 4 Calculation of Biallelic Pathogenic Mutation Burden by the Kit of the Present Invention 1. Biallelic Pathogenic Mutation Refers to the Inactivation of Both Alleles of a Homologous Recombination Gene in a Tumor Sample. Specific Determination Criteria are as Follows:

1) there is LOH on a wild-type allele, which is accompanied by a pathogenic germline mutation;
2) a pathogenic germline mutation and a pathogenic somatic mutation both occur;
3) there is LOH on a wild-type allele, which is accompanied by a pathogenic somatic mutation; and
4) two different pathogenic somatic mutations occur.

2. Annotation Results of SNV and INDEL Obtained in Step 2 of Example 2 were Determined According to the Rules in Step 1, and HRR Genes Meeting the Conditions were Counted to Obtain a Biallelic Pathogenic Mutation Burden.

Example 5 Calculation of CN Burden of Homologous Recombination Genes by the Kit of the Present Invention 1. Genes with CNVs Obtained in Example 2 were Determined According to CN as Follows: Those with a CN Greater than a Sum of an Average CN and a Triple Standard Deviation of the Baseline Samples or Less than a Difference Between an Average CN and a Triple Standard Deviation of the Baseline Samples were Counted to Obtain the CN Burden.

Example 6 Calculation of a Genomic Structural Variation Score by the Kit of the Present Invention 1. Design of Whole-Genome Targeted Sequencing (SNP-Panel) Probes
1) regions for designing genome probes were screened as follows: gaps and regions with low mappability on the genome were removed, and genomic regions that had a GC content higher than 60% and less than 30% and a length of 200 bp were removed;
2) regions that had a length of 120 bp and included three or more loci with an Asian heterozygosity greater than 0.5 were removed; and
3) snp loci in a 1,000 genomes database in the regions for designing probes were screened as follows: it was determined whether an Asian heterozygosity was greater than 0.5; it was determined whether Hardy-Weinberg equilibrium was reached; and an snp locus was extended by 100 bp on both sides and then aligned with the genome, with not more than 10 alignment positions.
2. Analysis of Allele-Specific CNs
2.1 Calculation of AI Scores of Regions Other than Centromeres and Telomeres Pre-processed NGS data of the tumor and baseline samples determined by SNP-panel obtained in Example 1 were used to count a coverage of each probe. Locally weighted regression (LWR) was used to correct the coverage of each probe. Then a corrected coverage was used to calculate a CN corresponding to each probe and an allele frequency of an SNP locus on each probe. Calculation formulas for normal samples are as follows:
Calculation Formula for CN ($cn_T$):

$$cn_T = 2^{log_2\left(\frac{C_T}{C_N}\right)} \times 2$$

Calculation Formula for Allele Frequency (BAF):

$$BAF = \frac{n_B}{cn_T}$$

Calculation Formulas for Tumor Cells in Samples with a Tumor Content of $\rho$ are as Follows:

$$cn_T = \frac{\left(2^{log_2\left(\frac{C_T}{C_N}\right)} \times 2 - (1-\rho) \times 2\right)}{\rho}$$

$$BAF = \frac{n_B}{cn_T}$$

where, $cn_T$ represents a CN of a single probe for a test sample, $C_T$ represents a coverage of the test sample on the probe, $C_N$ represents an average coverage of the baseline sample on the probe, BAF represents an allele frequency, and $n_B$ represents a CN of a genotype with a low allele frequency.

According to $cn_T$ and BAF values of all SNP-panel probes for each chromosome arm, the CBS method was used to segment based on $cn_T$ so that the chromosome arms were segmented into regions with equivalent CNs. The CBS method was used to further segment the obtained regions based on BAF into regions with equivalent allele-specific CNs, and CNs $n_B$ and $n_A$ of each genotype of each region were acquired. Cases where $n_B$ was equal to 0 and $n_A$ was not equal to 0 were counted to obtain AI scores of regions other than centromeres and telomeres (auto-AI-score).
2.2 Calculation of AI Scores of Telomeric Regions According to pre-processed data of tumor samples determined by WGS obtained in Example 1, the software ichorCNA was used to identify CNVs at a whole genome scale, the genome was divided into regions with CNs of 0, 1, 2, 3, 4, 5, and 6, and a ploidy P of tumor cells was evaluated. Telomeric and subtelomeric regions were determined according to the following criteria:
1) CN: 1, 3, and 5;
2) CN: not equal to the ploidy P; and
3) region length: not across centromeres.

Regions meeting the above criteria were counted to obtain AI scores of telomeric regions (TELO-AI-score).
2.3 Calculation of LST Scores Determination was conducted according to CNs of different regions on each chromosome arm calculated by the software ichorCNA in the previous step. Regions meeting the following conditions were counted and a resulting value was recorded as an LST-score:
1) continuous CNV region;
2) distance among regions: a specified threshold; and
3) length of a region itself: a specified threshold.
2.4 Calculation of Genomic Structural Variation Scores A genomic structural variation score (STV-score) was obtained by calculating a weighted or unweighted sum of one or more of TELO-AI-score, auto-AI-score, and LST-score.

Example 7 Scoring of a Genomic Homologous Recombination Pathway by the Kit of the Present Invention The scoring of a genomic homologous recombination pathway refers to using a statistical method or a machine learning method to score one or more of the pathogenic mutation of homologous recombination genes, the CN burden of homologous recombination genes, the mutational signature of homologous recombination genes, the biallelic pathogenic mutation burden of homologous recombination genes, and the genomic structural variation score obtained in Examples 2 to 6.

Example 8 Detection of the Lowest Detection Limit of Genome Instability by the Kit of the Present Invention 1. Preparation of Standards for the Lowest Detection Limit of Genome Instability 3 groups of paired tumor FFPE samples and normal tissue samples were adopted. DNA corresponding to normal cells was used to serially dilute paired tumor tissue DNA (tumor DNA contents after dilution were 40%, 30%, 20%, and 10%, respectively). A difference between an HRD score of a diluted tumor sample and an HRD score of an undiluted original sample was used to determine the requirement of SNP-panel for the lowest tumor fraction in the evaluation of genome instability. Information of the standards for the lowest detection limit of genome instability is shown in Table 4 below:

TABLE 4

Sample information for sensitivity verification of the HRD score of genome instability relative to tumor fraction

| Sample source | Number of cases | Purpose of verification |
|---|---|---|
| Healthy human blood cell (BC) | 40 | SNP Panel baseline |
| Known tissue samples with high HRD scores are serially diluted with corresponding normal tissue DNA to simulate different tumor cell fractions | 3 cases * 4 tumor fraction gradients * 15 replicates | the lowest detection limit of tumor fraction |

Figure 1:
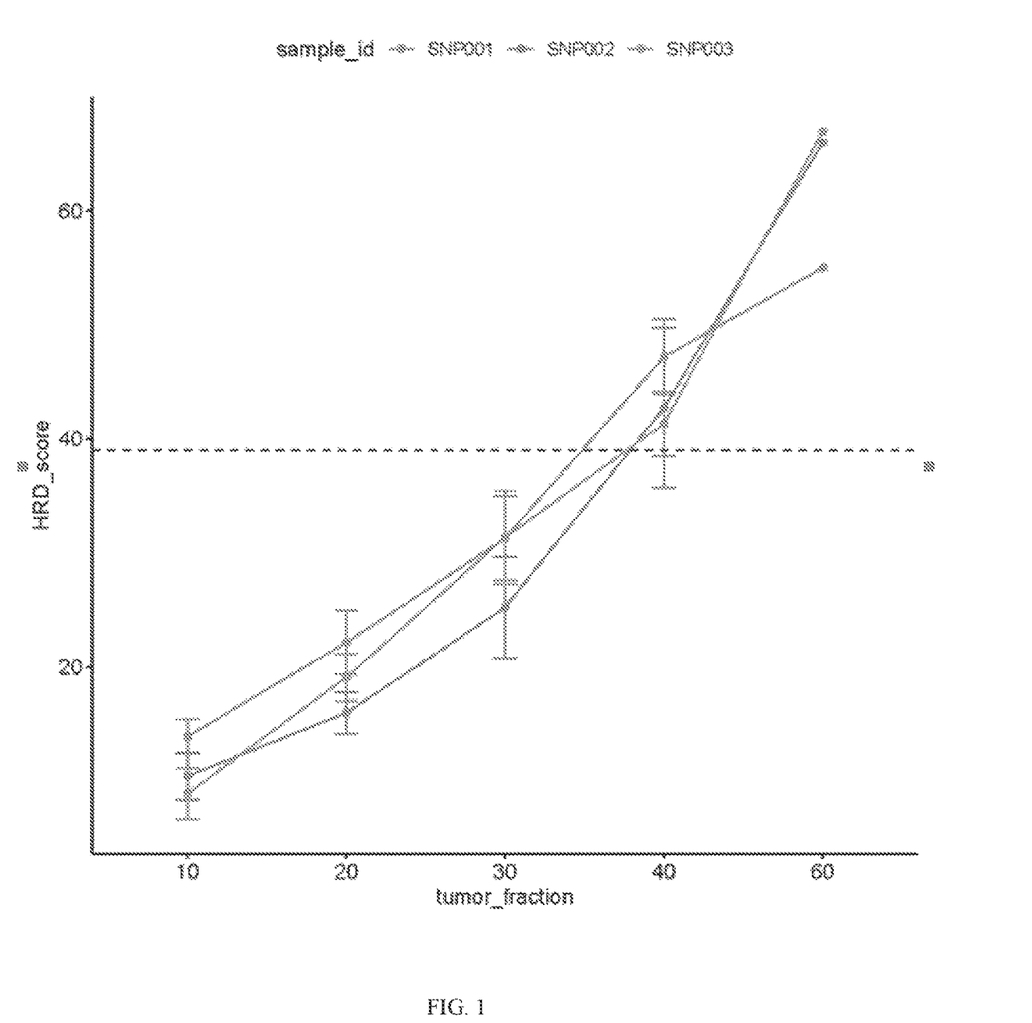
FIG. 1 shows results of the sensitivity verification of the BIRD score of genome instability relative to tumor fraction.

2. Experimental Procedures and Sequencing Data Processing can be Seen in Example 1, and Bioinformatics Analysis can be Seen in Example 6.
3. The Test was Repeated 20 Times
4. Experimental Results FIG. 1 shows results of the sensitivity verification of the BIRD score of genome instability relative to tumor fraction.

Results of the sensitivity verification of the HRD score of genome instability relative to tumor fraction

| sample no | tumor fraction (%) | mean · HRD score | sd · HRD score | n/N | PPA [CI95] |
|---|---|---|---|---|---|
| SNP001 | 10 (n = 15) | 13.87 | 1.51 | 0/15 | 0% [0%, 20.39%] |
|  | 20 (n = 15) | 22.13 | 2.80 | 0/15 | 0% [0%, 20.39%] |
|  | 30 (n = 15) | 31.27 | 3.71 | 1/15 | 6.67% [1.19%, 29.82%] |
|  | 40 (n = 15) | 47.20 | 3.30 | 15/15 | 100% [79.61%, 100%] |
| SNP002 | 10 (n = 15) | 10.40 | 2.06 | 0/15 | 0% [0%, 20.39%] |
|  | 20 (n = 15) | 15.93 | 1.83 | 0/15 | 0% [0%, 20.39%] |
|  | 30 (n = 15) | 25.20 | 4.49 | 0/15 | 0% [0%, 20.39%] |
|  | 40 (n = 15) | 42.73 | 7.05 | 11/15 | 73.33% [48.05%, 89.1%] |
| SNP003 | 10 (n = 15) | 8.87 | 2.23 | 0/15 | 0% [0%, 20.39%] |
|  | 20 (n = 15) | 19.07 | 2.09 | 0/15 | 0% [0%, 20.39%] |
|  | 30 (n = 15) | 31.33 | 4.10 | 0/15 | 0% [0%, 20.39%] |
|  | 40 (n = 15) | 41.33 | 2.85 | 12/15 | 80.00% [54.81%, 92.95%] |
| ALL40% | 40 (n = 45) | 43.76 | 14.14 | 38/45 | 84.44% [71.21%, 92.25%] |

Analysis results showed that the present invention exhibited high reproducibility and stability to the genome instability of samples with different tumor contents (>40%). Based on this analysis, the lowest detection limit of the kit of the present invention for evaluating genome instability was defined as: tumor cell content ≥40%.

Example 9 Detection of the Precision of the Kit of the Present Invention for Evaluating Genome Instability 1. Preparation of Standards for the Precision for Evaluating Genome Instability 5 clinical samples were adopted, where, 4 had a high HRD score and 1 had a low HRD score. The intra-batch and inter-batch reproducibility tests were conducted, separately. Due to the limited sample DNA, an initial volume of library building was designed as 50 ng for the 5 samples in this study. 3 replicates were set for a sample in the same batch, and 2 batches were adopted. Moreover, some samples were sequenced with 2 sequencers. An analysis platform in this part was targeted sequencing for SNP loci (SNP Panel). An HRD status threshold adopted a cut-off value calculated from a small cohort, that is, HRD score ≥39 indicates a high HRD status and HRD score <39 indicates a low HRD status. Information of the standards for the precision for evaluating genome instability is shown in Table 5 below:

TABLE 5

Sample information for precision verification of the HRD score of genome instability

| Sample source | Number of cases | Purpose of verification |
|---|---|---|
| Known tissue samples with high HRD scores | 4 cases * (4 library-building replicates * 1 sequencing point + 2 library-building replicates * 3 sequencing points) | Precision analysis |
| Known tissue samples with low HRD scores | 1 case * (4 library-building replicates * 1 sequencing point + 2 library-building replicates * 3 sequencing points) | |

2. Experimental Procedures and Sequencing Data Processing can be Seen in Example 1, and Bioinformatics Analysis can be Seen in Example 6.
3. The Test was Repeated 10 Times
4 Experimental Results Consistent results of precision research of the HRD score of genome instability

| Sample type | Variation type | n/N | PPA[95CI] |
|---|---|---|---|
| FFPE (n = 40) | HRD score High | 40/40 | 100% [91.24%-100%] |
| FFPE (n = 10) | HRD score Low | 10/10 | 100% [72.25%-100%] |

Example 10 Detection of the Accuracy of the Kit of the Present Invention for Evaluating Genome Instability 1. Preparation of Standards for the Accuracy for Evaluating Genome Instability Clinical samples of multiple cancer types were selected, 52 cases in total, including 15 cases of BRCA1/2 mutation samples and 37 cases of BRCA1/2 wild-type samples. The cancer types include breast cancer, ovarian cancer, colon cancer, rectal cancer, small-cell lung cancer (SCLC), and the like. In order to ensure the accuracy of an BIRD score and avoid the influence of a tumor fraction in a sample, a sample involved in the comparison was required to have a tumor cell fraction ≥40%. The consistency between the two platforms of WGS and SNP Panel in the present invention for detecting genome instability was analyzed. Information of the standards for the accuracy for evaluating genome instability is shown in Table 6 below:

TABLE 6

Verification samples for Genomic Scar of genome instability

| Sample source | Number of cases | Purpose of verification |
|---|---|---|
| Known BRCAm/ BRCAw FFPE tissue sample | 52 | correlation between an HRD score of SNP Panel and BRCA; correlation between an HRD score of Low Pass WGS and BRCA; Comparison of SNP panel with Low Pass WGS |

2. Experimental Procedures and Sequencing Data Processing can be Seen in Example 1, and Bioinformatics Analysis can be Seen in Example 6.

3. Experimental Results

Figure 2:
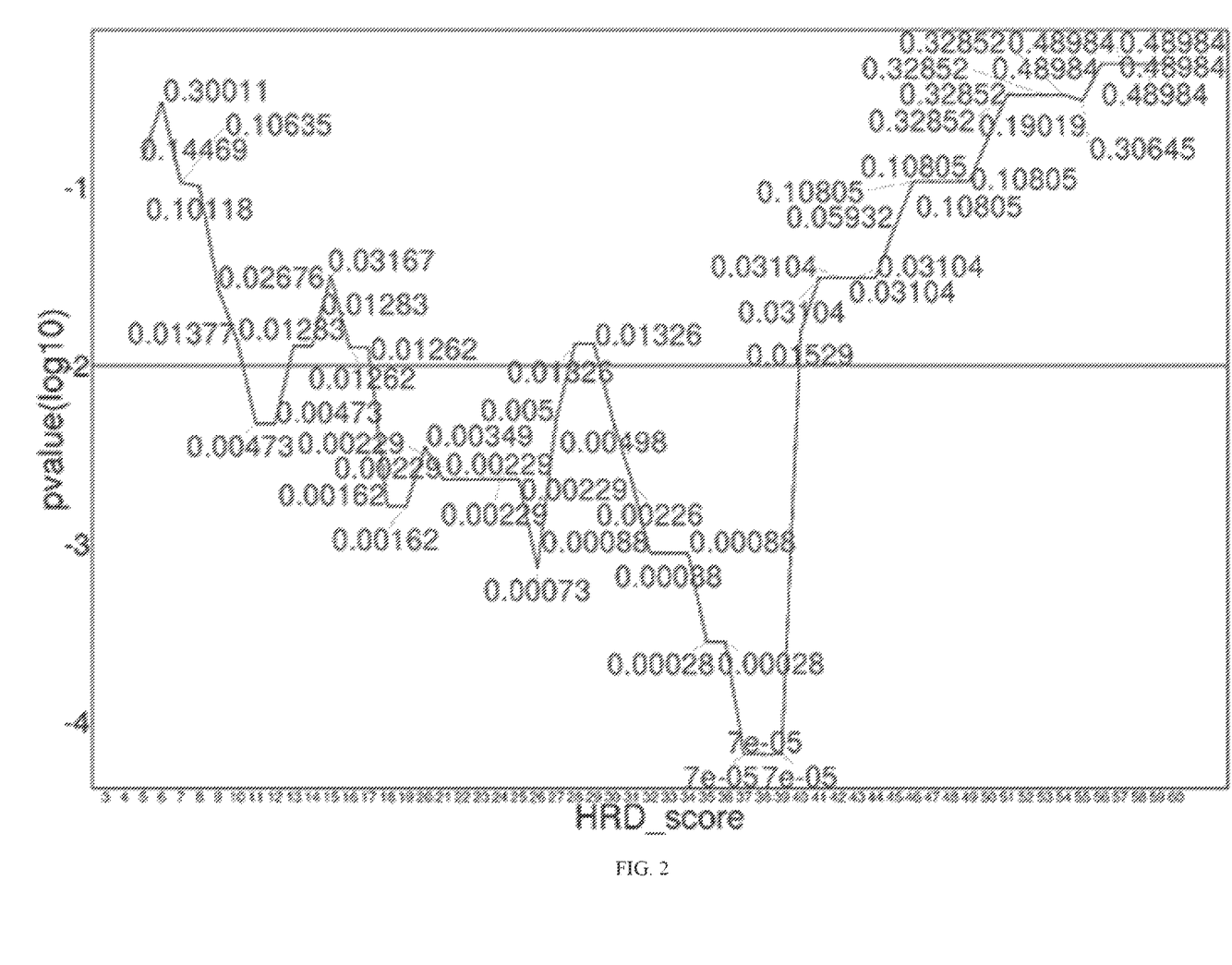
FIG. 2 shows a Fisher's test chart of genome instability of a multi-cancer cohort based on a WGS platform.
Figure 3:
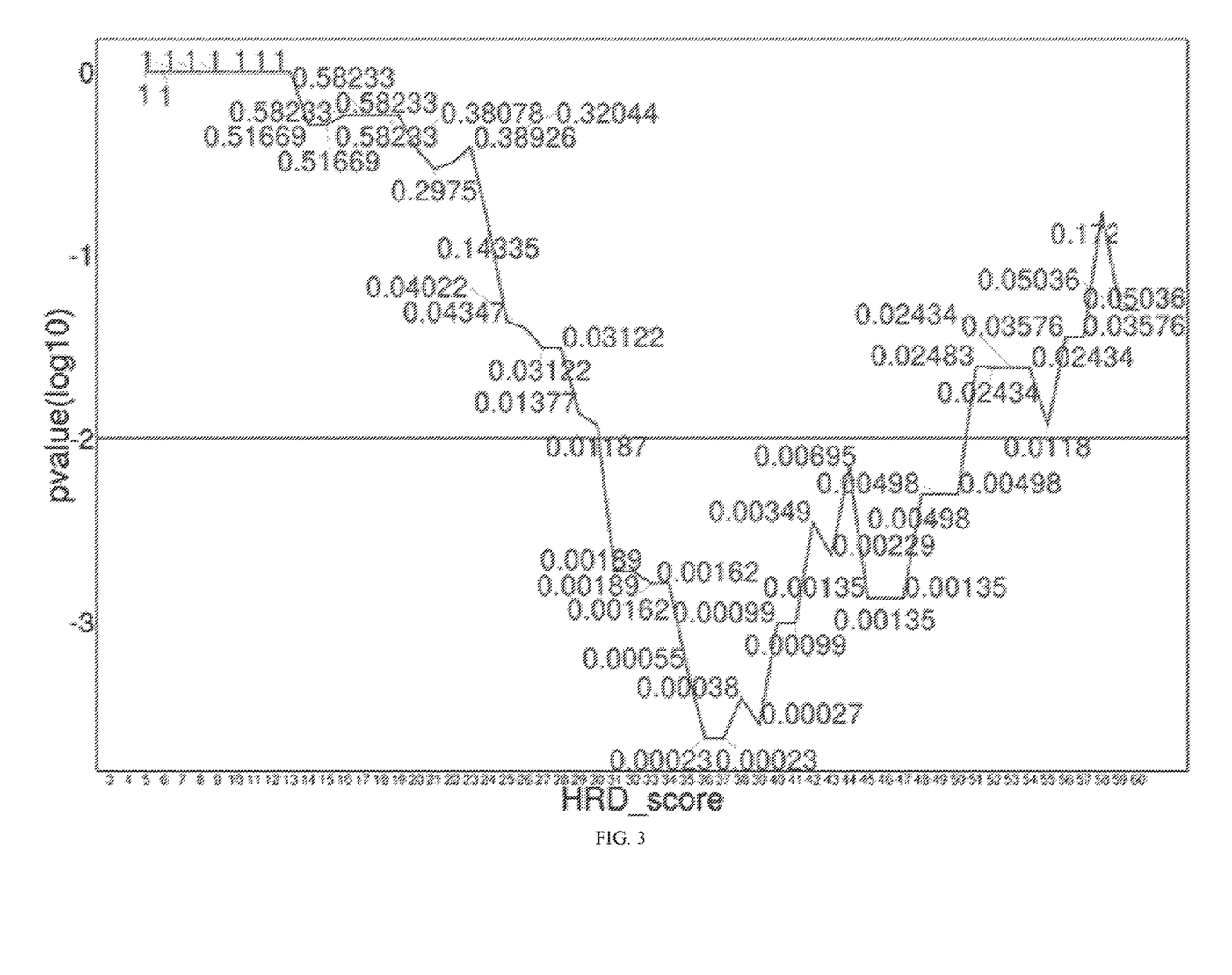
FIG. 3 shows a Fisher's test chart of genome instability of a multi-cancer cohort based on an SNP panel.

FIG. 2 shows a Fisher's test chart of genome instability of a multi-cancer cohort based on a WGS platform. FIG. 3 shows a Fisher's test chart of genome instability of a multi-cancer cohort based on an SNP panel.

Classification results of HRD scores based on WGS (threshold ≥ 39)

| | | BRCA status | | |
|---|---|---|---|---|
| | | Positive | Negative | Total |
| WGS Platform Cut-off: 39 | Positive | 8 | 1 | 9 |
| | Negative | 7 | 36 | 43 |
| | Total | 15 | 37 | 52 |
| Agreement Including Valid Results Only (Total N = 52) | PPA [95% CI] | 53.33% [30.11%, 75.19%] | | |
| | NPA [95% CI] | 97.3% [86.18%, 99.52%] | | |
| | OPA [95% CI] | 84.62% [72.48%, 91.99%] | | |

Classification results of HRD scores based on SNP panel (threshold ≥ 39)

| | | BRCA status | | |
|---|---|---|---|---|
| | | Positive | Negative | Total |
| SNP Panel Platform Cut-off: 39 | Positive | 12 | 8 | 20 |
| | Negative | 3 | 29 | 32 |
| | Total | 15 | 37 | 52 |
| Agreement Including Valid Results Only (Total N = 52) | PPA [95% CI] | 80% [54.81%, 92.95%] | | |
| | NPA [95% CI] | 78.38% [62.81%, 88.61%] | | |
| | OPA [95% CI] | 78.85% [65.97%, 87.76%] | | |

According to analysis results, the two platforms show prominent consistency.

What is claimed is:

1. A method for determining genome instability based on massively parallel next generation sequencing (NGS), wherein, the method is not used for a disease diagnosis, but for a determination based on a bioinformatics analysis, wherein the method is used to determine whether there is a lack of homologous recombination by calculating a comprehensive value of at least one selected from the group consisting of a pathogenic point mutation or an insertion/deletion (Indel) mutation of homologous recombination repair (HRR) genes, a biallelic pathogenic mutation burden of the HRR genes, a mutational signature of the HRR genes, a copy number variation (CNV) of the HRR genes, a copy number (CN) burden of the HRR genes, and a genomic structural variation, wherein the method specifically comprises the following steps:

1) Performing targeted sequencing on a tumor sample and a baseline sample based on the NGS, wherein the targeted sequencing comprises:
   obtaining a DNA library from the tumor sample and a DNA library from the baseline sample;
   designing probes for a single-nucleotide polymorphism (SNP)-panel as follows:
   a) removing gaps and regions with a low mappability on the human reference genome, and removing genomic regions having a length of 200 bp and a GC content, wherein the GC content is higher than 60% and less than 30%;
   b) removing regions having a length of 120 bp and comprising three or more loci that greater than 50% of an Asian population are heterozygous at; and
   c) screening SNP loci in a human genomic database in regions for designing the probes, excluding the regions previously removed, for the SNP-panel as follows: determining regions with the three or more loci that greater than 50% of an Asian population are heterozygous at, determining whether Hardy-Weinberg equilibrium is reached for the SNP loci being screened other than the three or more loci that greater than 50% of the Asian population are heterozygous at, removing or retaining each SNP locus within the SNP loci based on whether they have reached Hardy-Weinburg equilibrium and whether a sequence comprising the SNP and 100 bp extended on both sides of the SNP aligns with the human reference genome at 10 or less alignment positions;

performing a hybrid capture comprising: mixing a DNA library obtained from the tumor sample to obtain a tumor DNA library mixture and mixing a DNA library obtained from the baseline sample to obtain a baseline DNA library mixture, adding human Cot-1 DNA and blocking sequences to each DNA library mixture, and then subjecting each DNA library mixture to an evaporation drying with a vacuum centrifugal concentrator to obtain evaporated resulting DNA libraries;

performing a DNA hybridization with the probes to each evaporated resulting DNA library to obtain captured libraries and amplifying the captured libraries to obtain amplified captured libraries; and performing a library sequencing comprising: mixing the captured DNA library obtained from the tumor sample and the captured DNA library obtained from the baseline sample to obtain a resulting captured DNA library mixture, wherein the resulting captured DNA library mixture comprises a 6:1 ratio of tumor captured library to baseline captured library; and using a gene sequencer to conduct a library sequencing on the captured DNA library mixture on a computer to obtain sequencing data; after the library sequencing on the computer is completed, processing the sequencing data to obtain processed NGS sequences of the tumor sample and the baseline sample, wherein the processed NGS sequences are without adapters and primers and include HRR genes;

2) Obtaining pre-processed whole genome sequencing (WGS) data of the tumor sample and the baseline sample, and aligning the pre-processed WGS data of the tumor sample and the baseline sample and the processed NGS sequences of the tumor sample and the baseline sample with a human reference genome to obtain position information of each sequence, alignment quality information, and aligned results, analyzing the aligned results for quality evaluation, and using the aligned results to obtain a B-allele frequency (BAF) and a CN of each of a plurality of heterozygous loci in a targeted region of the tumor sample;

3) Screening out a heterozygous locus of the plurality of heterozygous loci of the tumor sample and acquiring an allele frequency of the heterozygous locus;

4) Determining allelic imbalance (AI) scores of telomeric regions and regions other than centromeres and telomeres in the genome, wherein:
   a) the AI scores of the regions other than the centromeres and the telomeres are calculated as follows: using the processed NGS sequences of the tumor sample and the baseline sample determined by the targeted sequencing in step 1 to, for each of the tumor sample and baseline sample: count a coverage of each probe of the probes; using locally weighted regression (LWR) to correct the coverage of each probe; and using the corrected coverage to calculate a CN corresponding to each probe and an allele frequency of a SNP locus on each probe,
   wherein calculation formulas for each probe for the baseline sample are as follows:
   calculation formula for CN ($cn_T$):

$$cn_T = 2^{\log_2\left(\frac{C_T}{C_N}\right)} \times 2;$$

calculation formula for the allele frequency (BAF):

$$BAF = \frac{n_B}{cn_T};$$

and
   calculation formulas for each probe for the tumor sample with a tumor content of $\rho$ are as follows:

$$cn_T = \frac{\left(2^{\log_2\left(\frac{C_T}{C_N}\right)} \times 2 - (1-\rho) \times 2\right)}{\rho}; \text{ and}$$

$$BAF = \frac{n_B}{cn_T},$$

wherein for each of the baseline sample and the tumor sample, $cn_T$ represents a CN of a single probe for a test sample $C_T$ represents a coverage of the test sample on the single probe, $C_N$ represents an average coverage of the baseline sample on the single probe, BAF represents the allele frequency, and $n_B$ represents a CN of a non-reference B allele in a germline heterozygous SNP,
   wherein for the calculation formulas for the baseline sample, the test sample refers to the baseline sample, and for the calculation formulas for the tumor sample, the test sample refers to the tumor sample;
   according to $cn_T$ and BAF values of all the probes for the SNP-panel for each chromosome arm included in the regions other than the centromeres and the telomeres for each of the tumor sample and the baseline sample, using a circular segmentation (CBS) method to perform a first segmentation based on $cn_T$ so that each chromosome arm is segmented into regions with equivalent CNs; using the CBS method to further segment the regions with the equivalent CNs based on BAF into regions with equivalent allele-specific CNs, and acquiring CNs $n_B$ and $n_A$ of each genotype of each region of the regions with the equivalent allele-specific CNs, wherein $n_A$ is a CN of reference A allele in the germline heterozygous SNP; and for each region, counting cases where $n_B$ is equal to 0 and $n_A$ is not equal to 0 to obtain the AI scores of the regions other than the centromeres and the telomeres (auto-AI-scores); and
   b) the AI scores of the telomeric regions are calculated as follows:
   using the pre-processed WGS data of the tumor sample telomeric regions and subtelomeric regions, identifying CNVs within the telomeric regions and subtelomeric regions and dividing the human reference genome into regions with CNs of 0, 1, 2, 3, 4, 5, or 6, within the telomeric regions and subtelomeric regions and evaluating a ploidy P of the tumor sample; determining regions meeting all the following criteria:
   I) CN of 1, 3, or 5;
   II) CN not equal to the ploidy P; and
   III) a region location not spanning across the centromeres; and
   counting the regions meeting the three criteria I, II, and III within each telomeric region and subtelomeric region to obtain the AI scores of the telomeric regions (TELO-AI-scores);
5) Using the pre-processed WGS data of the tumor sample and the baseline sample to obtain remaining sequences of regions in the tumor sample other than the telomeric regions and subtelomeric regions obtained in step 4b; and aligning the remaining sequences with the human reference genome, adding with the CNs determined for the telomeric regions and subtelomeric regions of the tumor sample in step 4b to obtain a CN of the tumor sample at the whole genome scale;
6) Using the results in step 5 to determine large-scale state transition (LST) scores,
   wherein the LST scores are calculated as follows: for each chromosome arm, according to the CNs of the telomeric regions on each chromosome arm calculated to identify CNVs, counting regions meeting all the following conditions: I) having continuous CNV regions, wherein the continuous CNV regions are adjacent genomic region intervals having the same CNs, and the telomeric regions have a continuous CNV across the entire region; II) having a distance among regions within a first specified threshold; and III) having a length of a region within a second specified threshold; and recording a resulting value as an LST-score for each chromosome arm; and
7) Obtaining a score for the genomic structural variation (STV-score) by calculating a weighted or unweighted sum of at least one selected from the group consisting of the TELO-AI-scores obtained in step 4b, the auto-AI-scores obtained in step 4a, and the LST-scores obtained in step 6;
8) Determining the mutational signature of HRR genes included in the processed NGS sequences from the targeted sequence data for the tumor sample based on statistics of targeted sequencing data of HRR genes obtained from the alignment results of the processed NGS sequences of the tumor sample and the baseline sample in step 2, comprising the following steps:
   a) identifying single-nucleotide variants (SNVs) and annotating at a genetic level to obtain annotation results;
   b) screening according to the annotation results; and
   c) analyzing the mutational signature; and
9) Determining the pathogenic point mutation or the Indel mutation of the HRR genes through the targeted sequencing data of the HRR genes obtained from the alignment results of the processed NGS sequences of the tumor sample and the baseline sample in step 2; determining the biallelic pathogenic mutation burden of the HRR genes based on a number of mutated alleles of each HHR gene; and determining the CN burden of the HRR genes by calculating a number of HRR genes in which the CNVs of the HRR genes exceed a threshold.

2. The method for determining the genome instability based on the NGS according to claim 1, wherein
the step of obtaining a DNA library from the tumor sample and a DNA library from the baseline sample comprises the following steps:
A) diluting formalin-fixed and paraffin-embedded tissue sample DNA (FFPE DNA) and blood sample DNA (BC DNA) to a concentration of 6 ng/μL, wherein the FFPE DNA is used as the tumor sample and the BC DNA is used as the baseline sample, and using a nucleic acid interrupter to treat each of the FFPE DNA and the BC DNA to obtain fragmented FFPE DNA and fragmented BC DNA, respectively;
B) adding the fragmented FFPE DNA and the fragmented BC DNA respectively to an end repair/A-tailing reaction system to obtain two first mixtures, and performing a first PCR to each of the two first mixtures to obtain two first PCR products including A-tailed fragmented FFPE DNA and A-tailed fragmented BC DNA respectively; after the first PCR is completed, adding ligation reagents to each of the two first PCR products to obtain two second mixtures and performing a second PCR to each of the two second mixtures to obtain two ligation PCR products, respectively; and after the second PCR is completed, conducting a first magnetic bead purification to each of the two ligation PCR products to obtain a purified ligation product of the FFPE DNA and a purified ligation product of the BC DNA; and
C) adding amplification reagents to each of the purified ligation product of the FFPE DNA and the purified ligation product of the BC DNA to obtain two first resulting mixtures, and conducting a third PCR on each of the two first resulting mixtures, each according to the following reaction procedure: 98° C. for 45 s for 1 cycle; 98° C. for 15 s, 60° C. for 30 s, 72° C. for 30 s, for N cycle; and 72° C. for 1 min for 1 cycle; terminating the third PCR of the two first resulting mixtures at 8° C. to respectively obtain two products of the third PCR, and conducting a second magnetic bead purification to each of the two products of the third PCR obtain an FFPE DNA library and a BC DNA library; using a nucleic acid concentration detector to quantify if the FFPE DNA library is ≥350 ng and the BC DNA library is ≥200 ng; and using a bioanalyzer to analyze the FFPE DNA library and the BC DNA library, wherein, main peaks are located between 150 bp to 500 bp, the FFPE DNA library is the DNA library obtained from the tumor sample, and the BC DNA library is the DNA library obtained from the baseline sample.

3. The method for determining the genome instability based on the NGS according to claim 2, wherein:
the end repair/A-tailing reaction system for the first PCR comprises: 2 μL of an end repair enzyme, 10 μL of an end repair buffer, and 48 μL of nuclease-free water; the first PCR is conducted at 20° C. for 30 min and at 65° C. for 30 min and then terminated at 4° C.; and
the ligation reagents for the second PCR comprise: 30 μL of a DNA ligation buffer, 3 μL of a DNA ligase, 0.5 μL of a ligation enhancer, 2.5 μL of an adapter, and 14 μL of nuclease-free water; and the second PCR is conducted at 20° C. for 15 min and then terminated at 4° C.

4. The method for determining the genome instability based on the NGS according to claim 2, wherein in step C),
in the third PCR on the first resulting mixture of the purified ligation product of the FFPE DNA, N of the N cycle is 8;
in the third PCR on the first resulting mixture of the purified ligation product of the BC DNA, N of the N cycle is 6;
the amplification reagents in step C) comprise 25 μL of a hot-start enzyme mixture and 5 μL of library amplification primers; and
the amplification reagents are added to 20 μL of the purified ligation product of the FFPE DNA and to 20 μL of the purified ligation product of the BC DNA.

5. The method for determining the genome instability based on the NGS according to claim 2, further comprising: before the library sequencing: subjecting the resulting captured DNA library mixture to a quantification with the nucleic acid concentration detector, a fragment size analysis with the bioanalyzer, and a molar concentration calculation; mixing 5 μL of a 4 nM of the resulting captured DNA library mixture with 5 μL of 0.2 N NaOH to obtain a fourth resulting mixture, and subjecting the fourth resulting mixture to a first vortexing for thorough mixing, a second centrifugation, and a denaturation at room temperature for 5 min; adding 990 μL of an HT1 buffer to terminate the denaturation to obtain a fifth resulting mixture, and subjecting the fifth resulting mixture to a second vortexing for thorough mixing and a third centrifugation to obtain a denatured captured product; and diluting the denatured captured product to a predetermined concentration for the library sequencing on the computer.

* * * * *